US006842008B2

United States Patent
Stearns et al.

(10) Patent No.: US 6,842,008 B2
(45) Date of Patent: Jan. 11, 2005

(54) GAS DETECTOR WITH MODULAR DETECTION AND DISCHARGE SOURCE CALIBRATION

(76) Inventors: Stanley D. Stearns, P.O. Box 55603, Houston, TX (US) 77255; Huamin Cai, 8850 Chimney Rock, Apt. 68, Houston, TX (US) 77096

(*) Notice: Subject to any disclaimer, the term of this patent is extended or adjusted under 35 U.S.C. 154(b) by 122 days.

(21) Appl. No.: 10/387,011

(22) Filed: Mar. 11, 2003

(65) Prior Publication Data
US 2004/0178800 A1 Sep. 16, 2004

(51) Int. Cl.[7] ............................................. G01N 27/62
(52) U.S. Cl. ....................... 324/464; 324/71.1; 73/28.02
(58) Field of Search ............................... 324/464, 71.1; 73/28.02

(56) References Cited

U.S. PATENT DOCUMENTS

| 5,394,091 | A | | 2/1995 | Wentworth et al. |
| 5,602,468 | A | * | 2/1997 | Harrington ................. 324/71.1 |
| 5,767,683 | A | | 6/1998 | Stearns et al. |
| 6,448,777 | B1 | * | 9/2002 | Abdel-Rahman et al. ... 324/464 |
| 6,509,562 | B1 | * | 1/2003 | Yang et al. .................. 250/287 |

* cited by examiner

Primary Examiner—N. Le
Assistant Examiner—Timothy J. Dole
(74) Attorney, Agent, or Firm—Keeling Hudson, L.L.C.; Kenneth A. Keeling; James E. Hudson, III

(57) ABSTRACT

A pulsed discharge detector includes a device and method for modular measurement of ionization signals from a sample. The pulsed discharge detector includes a discharge source in a chamber, a collector spaced from the discharge source, a monitor connected to a discharge electrode, an electrometer connected to the collector, a calibrator and a sample and hold processor. The discharge electrodes include a source electrode centrally located in relation to the discharge chamber wall. The collector is centrally located in relation to the chamber wall. Discharge signals are monitored for time and intensity. Collected signals are adjusted based on the discharge intensity. Collected signals are collected during a time window based on the discharge occurrence time. Detector output is predicated on collected signals coordinated with pulsed discharges. The calibrator of the present invention adjusts the collected signals to reduce discharge noise. The sample and hold processor accumulates selected adjusted signal values to quantify sample concentrations.

29 Claims, 4 Drawing Sheets

GAS DETECTOR WITH MODULAR DETECTION AND DISCHARGE SOURCE CALIBRATION

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of Invention

The present invention is directed to detectors for measuring concentrations of a gaseous sample, and more particularly directed toward a pulsed discharge detector that correlates collected data with the discharge and calibrates collected data to reduce effects of discharge noise.

2. Related Art

Various forms of detectors are used to quantify constituents of a sample gas. Known detectors vary in how they make the sample detectable, arrange the necessary components of the detector, actually detect characteristics of the sample and process the detected data.

Pulsed discharge detectors ionize a discharge gas in a chamber to produce photons, introduce a sample gas to be tested and measure ionization currents of electrons produced from interaction of the photons with the sample gas. The ionization source of the detector is an electrical discharge in a discharge gas. The discharge gas may be a noble gas or a combination of noble gases.

As a test instrument, a pulsed discharge detector may be provided with a sample input gas eluted from a gas chromatograph column or other suitable source. The column effluent normally includes a carrier gas which is routinely input through the column at a specified flow rate. The column elutes the various constituents in peaks of concentration in a specific timed sequence, dependent on volatility of the sample constituents.

The gas chromatograph column separates compounds but does not quantify the concentrations of the compounds. Gas chromatograph detectors are connected downstream the column for quantitative analysis. By using a series of calibration gases, a fixed flow rate, and a specific stationary phase material, the gas chromatograph column can be used to separate compound types based upon the retention time. There may be any number of eluted peaks formed by the gas chromatograph column output to be quantified.

The ionization mechanism of a pulsed discharge detector is primarily photo-ionization wherein an electric discharge generates diatomic molecular emissions of photons. The high-energy photons in turn ionize the sample compounds in the detector chamber. When the pulsed discharge detector uses helium as the discharge gas, the photon generation process includes the following steps:

1. The electrical discharge ionizes some helium atoms, He, to helium ions, $He^+$.
2. The $He^+$ ions combine with helium atoms, He, to form diatomic molecular ions, $He_2^+$.
3. Each diatomic ion, $He_2^+$, captures one electron, dissociating back to two helium atoms, 2 He, emitting photons in the process.

During step 3, a continuous photon emission arises from the molecular interaction—the transition of diatomic helium molecular ions to ground state helium. These photons have an energy level in the range of 13.5~17.5 eV, which can ionize almost all compounds, except helium itself. Other processes of molecular interaction may also affect the electrical discharge, such as helium atomic emission and helium meta-stable generation.

Pulsed discharge detectors possess favorable characteristics over other gas chromatograph detectors. First, sensitivity is higher. The minimum detectable limit of gases present in a sample using a regular pulsed discharge detector in helium ionization detector mode is about 10 times lower than the minimum detectable limit identifiable using a flame ionization detector. Pulsed discharge detectors are operable to determine concentrations at the parts-per-billion level. Second, pulsed discharge detectors offer selectivity in response. Pulsed discharge detectors have a universal response when helium is used as the discharge gas. When helium is doped with another noble gas as the discharge gas, pulsed discharge detectors may have a selective response. Third, pulsed discharge detectors have a uniform response factor. Within an organic group the response factor increases linearly with the carbon number of the sample. Fourth, the pulsed discharge detector system does not require use of radioactive material.

Wentworth, et al. U.S. Pat. No. 5,394,091, teaches an ionization detector adapted for use in either helium ionization or electron capture mode. The detector utilizes a helium flow through a detector cell or chamber. The chamber has regions of spark discharge, sample introduction and sample detection. The helium flow is the only flowing material in the immediate region of the spark. A sample gas and/or carrier gas are injected and commingled with the helium gas downstream from the spark in the sample introduction region. Two electrodes, of which one is bias, detect the charged characteristics of the sample, the bias electrode at or upstream of the sample inlet and the other electrode downstream from the sample inlet. An electrometer measures the difference between the resulting currents. These current measurements are recorded on a timed basis. A base line current is formed as a result of impurities in the discharge or carrier gas.

Stearns, et al. U.S. Pat. No. 5,767,683, teaches a pulsed discharge detector having a bias voltage feedback system. The feedback system compares output from an electrometer connected to the collector electrode with a reference current using a comparison circuit. Output from the comparison circuit is input to a control circuit, which, in turn, outputs a bias voltage. The bias voltage is applied to the first bias electrode such that the electron current flow within the detector chamber remains constant for all concentrations of input sample gas. The instantaneous setting of the control circuit is used to form a second output. The magnitude of this second output is proportional to the concentration of a selected sample gas within the electron capture detector chamber and is the response signal of the disclosed electron capture detector system. Pulsed discharge detectors provide intermittent electrode discharges. A typical discharge voltage is in the range of 300 to 400 volts. A typical time interval between discharges is in a range of 100 microseconds to 800 microseconds.

Current pulsed discharge detectors measure, on a continuous basis, the current output of the sample gas, including readings during discharge events and including readings during the interval between pulses.

Sensitivity of measurement results is adversely affected by discharge variations, referred to as discharge noise.

Discharge noise can be reduced by a high quality pulser and a clean discharge electrode surface, but cannot be eliminated.

In prior art pulsed discharge detectors, a relatively short discharge period (interval between discharges) increases the sensitivity of the measurement. However, a relatively short interval between discharges results in increased average electrode temperatures and relatively short electrode life cycle.

The present invention provides an improvement to the prior art by increasing sensitivity of the pulsed discharge detector by providing a device and method to measure ionization signals in the sample gas modularly at the time of the discharge event as opposed to a collected current, by a geometric configuration that enhances collection of signals and by providing a means of calibrating collected signals to account for discharge noise.

The present invention accordingly provides an improvement to the prior art by allowing longer pulse periods, thereby reducing power requirement of a pulsed discharge detector and providing relatively longer product life.

The reduced power requirements of the detector of the present invention makes the detector particularly useful as a portable detector.

BRIEF SUMMARY OF THE INVENTION

A pulsed discharge detector includes a device and method for modular measurement of ionization signals from a sample. The pulsed discharge detector includes a discharge source in a chamber, a collector spaced from the discharge source, a monitor connected to a discharge electrode, an electrometer connected to the collector, a calibrator and a sample and hold processor. The discharge electrodes include a source electrode centrally located in relation to the discharge chamber wall. The collector is centrally located in relation to the chamber wall. Discharge signals are monitored for time and intensity. Collected signals are adjusted based on the discharge intensity. Collected signals are collected during a time window based on the discharge occurrence time. Detector output is predicated on collected signals coordinated with pulsed discharges. The calibrator of the present invention adjusts the collected signals to reduce discharge noise. The sample and hold processor accumulates selected adjusted signal values to quantify sample concentrations.

Accordingly, the objects of this invention are to provide, among other things, a pulsed discharge detector and method of operation that:

- adjusts the detected values for variations in intensity of the corresponding individual discharges;
- isolates the collected ionization signal from each particular discharge;
- integrates the resulting ionization signals from each discharge in order to establish concentration of the sample; and
- minimizes power consumption allowing for portability of the detector.

Other objects of this invention will become evident throughout the reading of this application.

DESCRIPTION OF THE INVENTION

Figure 1:
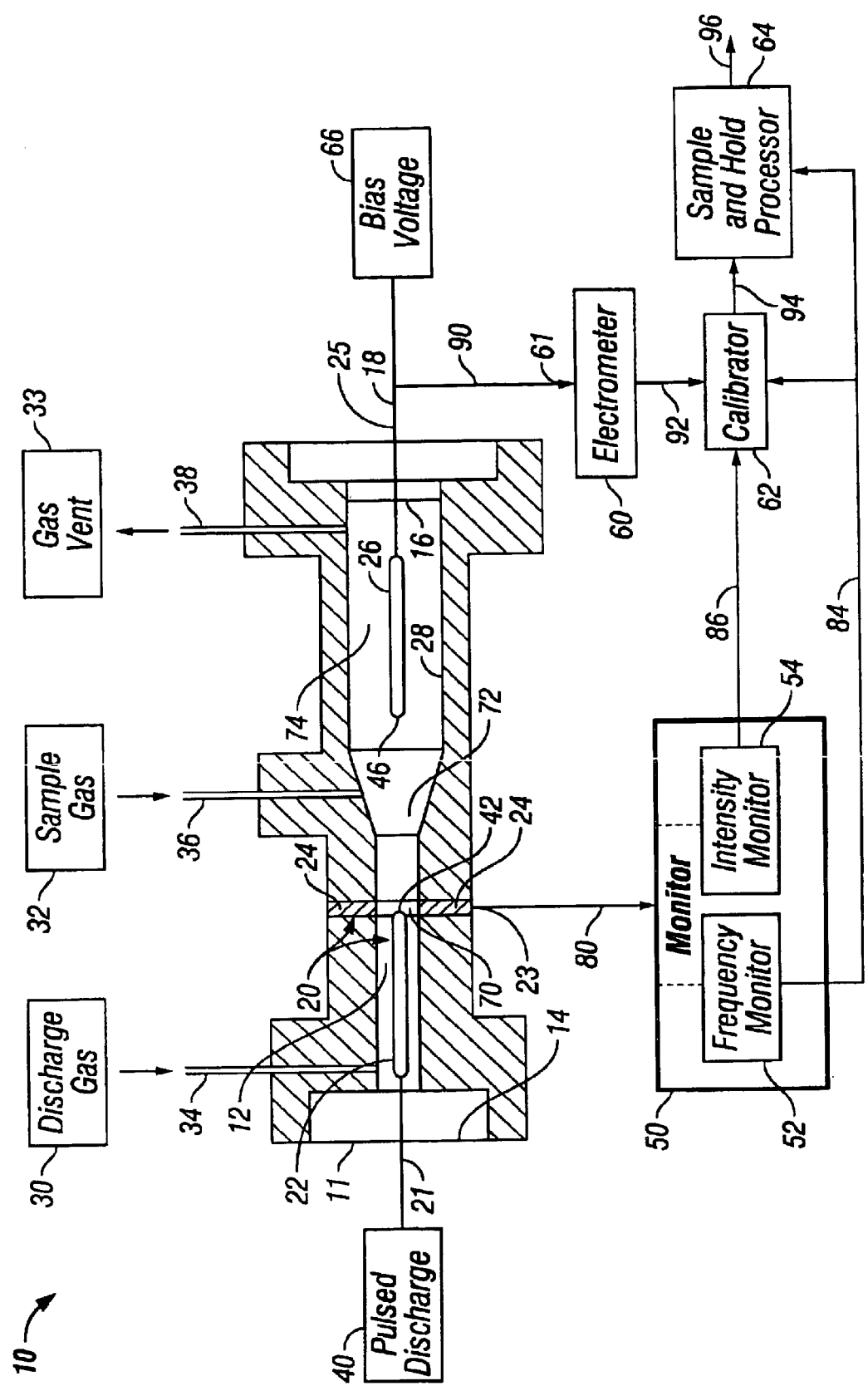
FIG. 1 is a cross-sectional view of a detector of the present invention, including a schematic depiction of components.

Referring to FIG. 1, detector 10 of the present invention is depicted. Detector 10 is typically integrated into an analytical system. Devices such as a gas chromatograph column (not shown) are typically used upstream of detector 10 to provide a sample gas (not shown), and other devices, such as a computer with interpretation software (not shown), are used to receive, store, manipulate and report generated data. A primary purpose of detector 10 is to determine the quantities of compounds in a sample gas.

Detector 10 includes closed chamber 12 within detector housing 11. In the exemplary embodiment, chamber 12 is an elongated hollow space in housing 11, oriented lengthwise along chamber axis 18. One end of chamber 12 is discharge end 14 and the other is collector end 16.

An electrical discharge source 20 is located proximate discharge end 14. In the exemplary embodiment, discharge source 20 includes source electrode 22 and receptor electrode 24. Source electrode 22 extends into chamber 12 proximate discharge end 14 of housing 11. Tip 42 of source electrode 22 is located at the central axis 18 of cylindrical chamber 12. In a preferred embodiment, source electrode 22 extends through discharge end 14 at the center of discharge end 14 and is arranged co-axially with the central axis 18 of chamber 12. Electrical source connection 21 is located outside housing 11 and provides an electrically conductive link of source electrode 22 to a power source (not shown). Receptor electrode 24 is emplaced circumferentially in the wall of housing 11, proximate tip 42 of source electrode 22. In a preferred embodiment, receptor electrode 24 extends circumferentially about cylindrical chamber 12. Electrical receptor connection 23 is located outside housing 11 and provides an electrically conductive link to receptor electrode 24. The configuration of tip 42 in relation to electrode 24 allows tip 42 to be equally distant from electrode 24 surfaces.

Collector 26 extends into chamber 12 proximate collector end 16. Collector tip 46 is located at the central axis 18 of cylindrical chamber 12. In a preferred embodiment, collector 26 extends through collector end 16 at the center of collector end 16 and is arranged co-axially with the central axis 18 of chamber 12. Accordingly, collector 26 is equally distant from chamber wall 28. Electrical collector connection 25 is located outside housing 11 and provides an electrically conductive link to collector 26.

In an exemplary embodiment, source electrode 22 and collector 26 are each elongated members aligned along axis 18. Collector tip 46 is spaced from source electrode tip 42.

Chamber 12 includes discharge region 70, expansion region 72 and collection region 74. Each discharge region 70, expansion region 72 and collection region 74 have circular cross-sections. The diameter of the collection region 74 is greater than the diameter of discharge region 70. The diameter of expansion region 72 increases from its interface with discharge region 70 to its interface with collection region 74. Discharge region 70 extends from end 14 of chamber 12 past tip 42. Collector region 74 extends from end 16 of chamber 12 past collector tip 46.

A discharge gas inlet 34 is provided proximate discharge end 14 to allow the introduction of discharge gas 30 into chamber 12 at discharge region 70. Discharge gas 30 may be helium, other suitable discharge gases known in the art, or combinations thereof. Discharge gas inlet 34 connects to a pressurized supply (not shown) of discharge gas 30. In the exemplary embodiment, discharge gas inlet 34 opens into chamber 12 intermediate discharge end 14 and source electrode tip 42.

A sample gas inlet 36 accesses chamber 12, in expansion region 72 to provide for introduction of a sample gas 32 (not shown). Sample gas inlet 36 is connected to a source of sample gas such as a gas chromatograph column (not shown).

In the exemplary embodiment, sample gas 32 includes a carrier gas, typically helium, and a volume of a sample matter. The detector identifies such sample matter in sample gas 32 as variations from the carrier gas.

Gas vent 38 is provided at the collector end 16 of chamber 12. In the exemplary embodiment, gas vent 38 penetrates housing 11 in collector region 74 proximate collector end 16 intermediate collector tip 46 and collector end 16.

The chamber 12 accordingly comprises a relatively narrow discharge region 70 with discharge gas inlet 36, a conical expansion region 7 with a sample gas inlet 36 and a cylindrical collector region 74 with a gas vent 38. Collector region 74 is relatively wider than inlet region 70. Such construction enhances flow of gases within chamber 12 from end 14 toward end 16. In operation, such configuration prevents direct contact of sample gases introduced at sample gas inlet 36 with discharge source 20.

Electrometer 60 is attached to electrical connection 25, electrically linking electrometer 60 to collector 26. In the exemplary embodiment, a bias voltage 66 is applied to electrical connection 25 thereby providing bias voltage 66 to collector 26 and to electrometer 60.

Electrometer 60 is electrically connected to calibrator 62. Calibrator 62 is electrically connected to sample and hold processor 64.

Electrical receptor connection 23 provides an electrically conductive link from receptor electrode 24 to monitor 50, comprising frequency monitor 52 and intensity monitor 54. Frequency monitor 52 and intensity monitor 54 are each electrically connected to calibrator 62 and to sample and hold processor 64.

In operation, discharge gas inlet 34 is connected to a discharge gas supply line (not shown), sample gas inlet 36 is connected to a sample gas supply line (not shown) and gas vent 38 is connected to a gas vent line (not shown). The lines and detector 10 create a sealed environment. The system is then filled with a discharge gas 30 such as helium.

A steady flow of discharge gas 30 is introduced through discharge gas inlet 34. The discharge gas 30 flows into chamber 12 and passes through chamber 12, exiting gas vent 38. Since sample gas inlet 36 is filled and pressurized with sample gas 32, the only available flow path for discharge gas 30 is through the length of chamber 12 and then gas vent 38. The only means for any substance to enter chamber 12 is through discharge gas inlet 34 and sample gas inlet 36, and the only matter that enters chamber 12 is discharge gas 30 and sample gas 32.

Once discharge gas 30 is flowing through chamber 12, pulsed high voltage discharge 40 is applied to electrical connection 21 creating a spark discharge intermediate source electrode 22 and receptor electrode 24. The spacing of source electrode 22 and receptor electrode 24 and the voltage level are arranged to cause ionization of discharge gas 30 particles generating diatomic molecular emissions of photons (not shown). As the configuration of chamber 12 forces flow from inlet 34 toward vent 38, the ionized discharge gas 30 particles are conveyed toward sample gas inlet 36 and in turn ionize compounds of sample gas 32 in expansion region 72 and collector region 74.

Figure 2A:
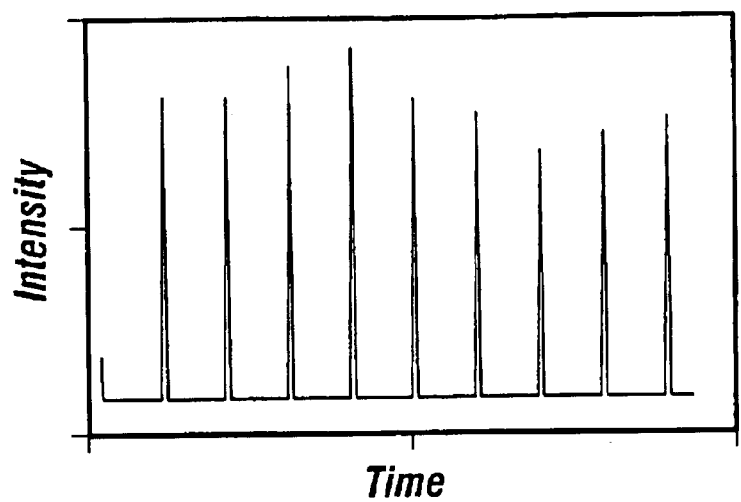
FIG. 2A is a graphical depiction of a monitored discharge signal overtime.

Pulsed discharge 40 results in a discharge signal 80 at receptor electrode 24. FIG. 2A comprises a graphical representation of discharge signal 80 over time.

Although pulsed discharge 40 is designed to produce a clean, distinct and discharge signal 80 with each repetition of pulsed discharge 40, variations in intensity occur. Such variations are commonly referred to as "noise."

In an exemplary embodiment, discharge signal 80 is transmitted to discharge monitor 50, comprising both frequency monitor 52 and intensity monitor 54. Frequency monitor 52 identifies synchronizing frequency signal value 84, including a discharge time and a discharge period, comprising the interval between pulsed discharges 40. Intensity monitor 54 identifies intensity signal value 86 at receptor electrode 24 for each pulsed discharge 40. Frequency signal value 84 and intensity signal value 86 may be individually or collectively transmitted to calibrator 62 and sample and hold processor 64.

Bias voltage 66 is applied to collector 26 through electrical connection 25. Such bias voltage 66 enhances reception of charged sample gas ions at collector tip 46. Bias voltage 66 may be positive or negative depending on the design of the detector. The amount of voltage used depends on the size of the detector.

Collected signal 90 is quantified by electrometer 60. Bias voltage 66 provides a measurement reference point. Bias voltage 66 variations create noise in collected signal 90. Applying bias voltage 66 directly to input lead 61 of electrometer 60, where electrical connection 25 connects with electrometer 60, minimizes such noise. Electrometer 60 produces collected signal value 92 from collected signal 90 and bias voltage 66.

Figure 2B:
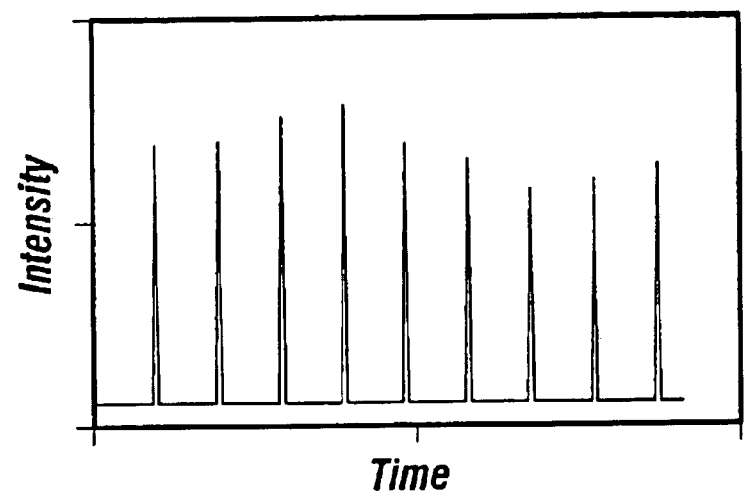
FIG. 2B is a graphical depiction of the collected signal overtime as in FIG. 2A.

Referring to FIG. 2B, intensity of collected signal value 92 over time is depicted. Collected signal value 92 is transmitted to calibrator 62. Calibrator 62 adjusts collected signal value 92 based on intensity signal value 86, producing adjusted signal value 94. Such adjustments include compensation for pulse discharge 40 noise.

In a preferred embodiment such adjustments are made during a time window coordinated with pulse discharge 40 events. Such temporal adjustments are made during a time window beginning with the discharge event and extending for a period of time that is determined by the user, such period of time being sufficient for ionized sample matter to be identified. Calibrator 62 may include digital circuitry or a microprocessor to adjust the duration of the collection window.

Figure 2C:
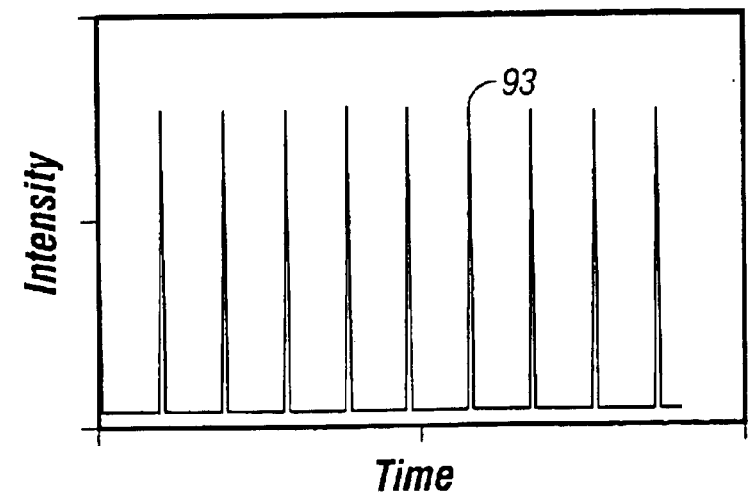
FIG. 2C is a graphical depiction of the adjusted signal overtime as in FIG. 2A.

Referring to FIG. 2C, a graphical depiction of the intensity of adjusted signal value 94 over time is depicted. The graphical depiction of FIG. 2C represents signal value 94 for a discharge gas 30, but does not indicate the elevated peaks that would be associated with matter in sample gas 32. Adjusted signal value 94 is transmitted to sample and hold processor 64, which quantifies the desired components of adjusted signal value 94, such desired components correlating to pulsed discharges 40 and disregarding signals intermediate pulsed discharge 40 events.

In an alternative embodiment, intensity signal value 86 may not be measured, but treated as a constant signal value 86. In such alternative embodiment, the collected signal 92 is collected during a time window initiated in response to a pulse discharge 40. In such alternative embodiment, the sensitivity of the resultant measurement will be decreased as compared to the sensitivity of the preferred embodiment disclosed. However, such alternative embodiment provides an improved measurement method over the prior art as such embodiment incorporates the advantages of modular identification of charged particles as opposed to determination of average induced current.

In the exemplary embodiment, sample and hold processor 64 accumulates the total value of adjusted collected value 94 for each pulse discharge 40. This process can also be accomplished through integration of adjusted collected value 94.

Frequency signal value 84 provides a timing mechanism for sample and hold processor 64 and for calibrator 62. Frequency signal value 84 may be a digital output that comprises a series of on/off pulses with the on pulses proportional to the pulsed discharge event 40. In a preferred embodiment, frequency signal value 84, in the on pulse condition, triggers collection of signal 94 by sample and hold processor 64 and triggers collection of collected signal 92 by calibrator 62. More specifically, with reference to calibrator 62, the on pulse condition triggers start of the time window during which calibrator 62 accumulates and adjusts the collected signal 92. Accordingly, the interval between collection events of signal 94 collected signal 92 by calibrator 62 vary according the interval between pulse discharges 40.

Figure 2D:
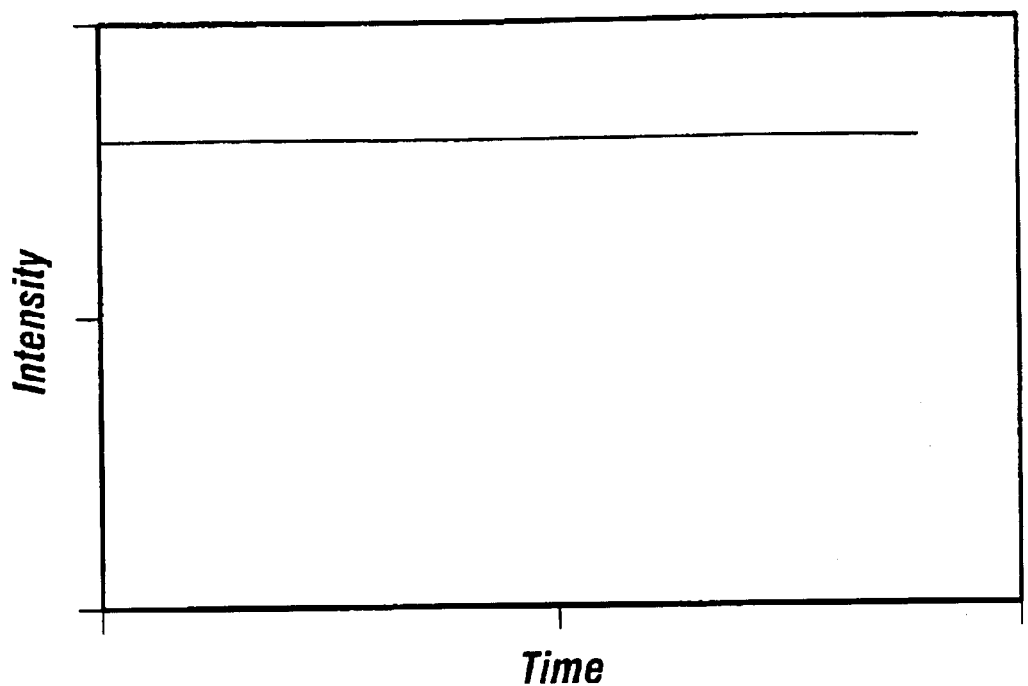
FIG. 2D is a graphical depiction of the output signal overtime as in FIG. 2A.

Referring to FIG. 2D, the accumulated values 96 are represented over time. The graphical depiction of FIG. 2D represents signal value 96 for a discharge gas 30, but does not indicate the elevated peaks that would be associated with sample gas 32. Such signal value 96 comprises an accumulation of peaks 93 as displayed in FIG. 2C.

Figure 2E:
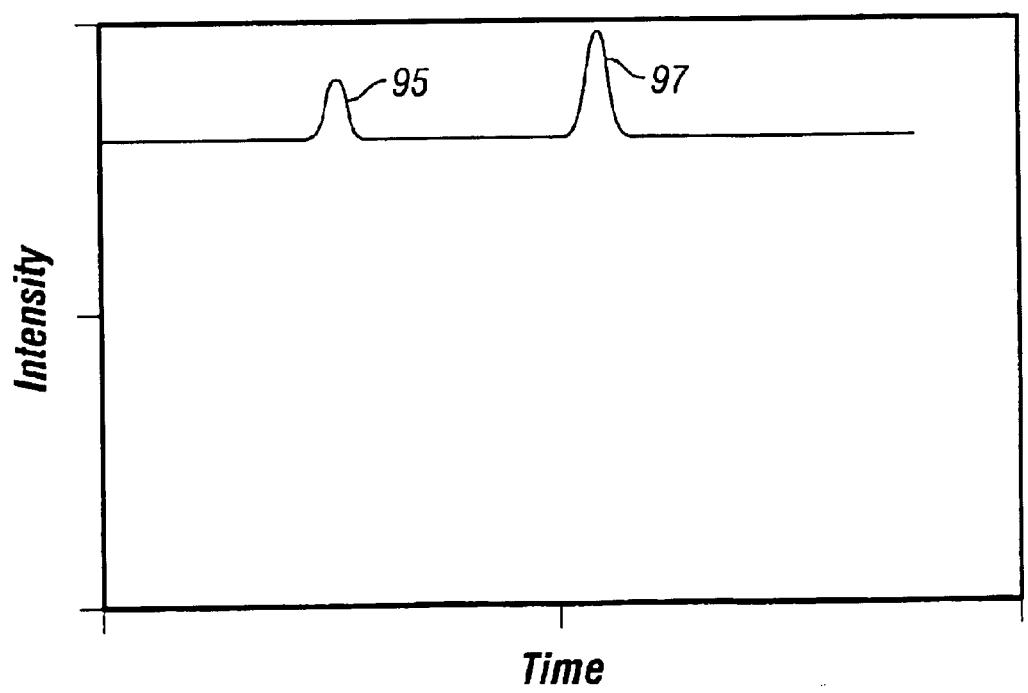
FIG. 2E is a graphical depiction of an output signal over time indicating concentration of sample compounds.

Referring to FIG. 2E, accumulated values 96 are represented over time with the occurrence of two compounds to be measured as resultants over time with peak 95 representing one compound and peak 97 representing a second compound.

It is noted in relation to FIGS. 2A through 2E that the time periods represented in FIGS. 2A, 2B and 2C are significantly shorter than the time periods represented in FIGS. 2D and 2E. Time periods represented in FIGS. 2A, 2B and 2C involve measurements in microseconds or milliseconds while time periods represented in FIGS. 2D and 2E involve measurements in minutes.

Collected signals 90 are nearly uniform when produced by pure discharge gas 30. Initiating the detection process with discharge gas 30 and sample gas 32 (consisting of only carrier gas) develops baseline values for collected signal 90, collected signal value 92, adjusted signal value 94 and accumulated values 96. Variations to these baseline values identify other sample matter (not shown) in sample gas 32.

The degree of variation in collected signal 90 and resultant values (collected signal value 92, adjusted signal value 94 and accumulated values 96) indicate concentration of matter in sample gas 32.

Figure 3:
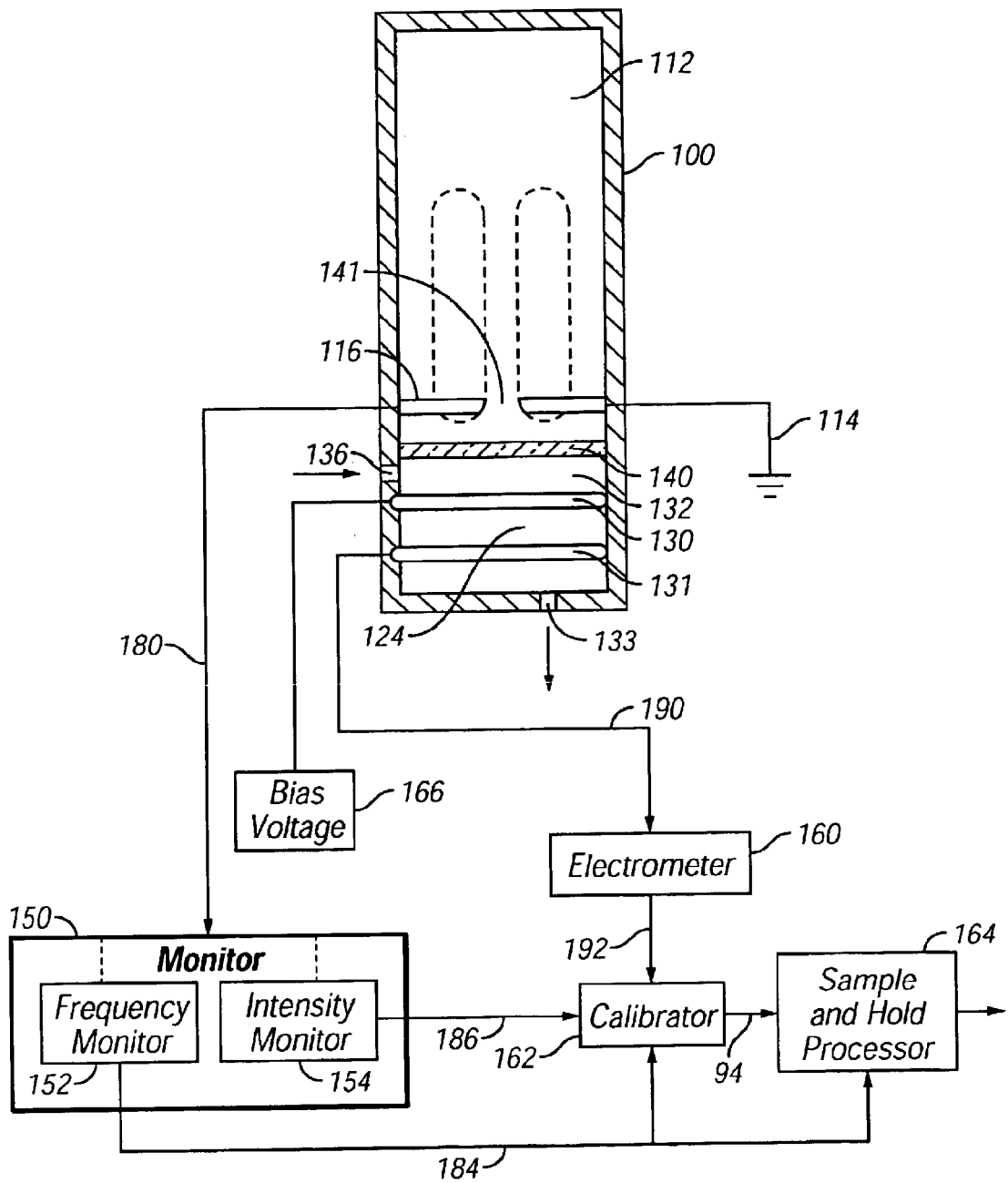
FIG. 3 is a cross-sectional view of an alternative embodiment incorporating the components of the present invention.

Referring to FIG. 3, an alternative embodiment of the present invention comprises monitor 150 consisting of frequency monitor 152 and intensity monitor 154, calibrator 162, sample and hold processor 164, electrometer 160 and bias voltage 166 applied to a gas sampling apparatus 100 including a sealed spark chamber 112 with a separate detector chamber 124. The construction and operation of apparatus 100 is disclosed in U.S. Pat. No. 5,528,150 issued to Stearns, et al. The apparatus 100 incorporates photoemission in a carrier gas, preferably helium and krypton, from a pulsed direct current, referred to herein as pulse discharges 141 across electrodes 114 and 116. Referring to FIG. 3, electrodes 114 and 116 comprise discharge electrode 114 and receptor electrode 116. Electrode 131 is grounded and electrode 130 is provided with a bias voltage 166 sufficient to attract desired charged particles created within sample chamber 124. A window membrane 140 is transparent to photoemission generated within the spark chamber 112. A sample gas 132 is exposed to such photoemissions through window membrane 140. Sample gas 132 enters through inlet 136 and exits through outlet 133. Photons generated by pulse discharges 141 energize the sample gas 132 and compounds therein producing free electrons from compounds in the sample gas 132. Free electrons are identified at electrode 130 with the magnitude of electrons proportional to the concentration of the compound to be quantified. The teachings of the preferred embodiment of the present invention are readily applied to the apparatus 100. Pulse discharges 141 generate a pulse signal 180 which is monitored by monitor 150 including frequency monitor 152 and intensity monitor 154. Frequency signal value 184 and intensity signal value 186 are transmitted to calibrator 162. Collected signal 190 is transmitted to electrometer 160 and collected signal value 192 is transmitted to calibrator 162. Calibrator 162 adjusts collected signal value 192 based on frequency signal value 184 and based on intensity signal value 186, producing adjusted signal value 194. Such adjustments include compensation for pulse discharge 141 noise. Such adjustments include temporal adjustments to co-ordinate signal value 192 collection time with pulse discharge 141 events. Sample and hold processor 164 accumulates the total value of adjusted collected values 194 for each pulse discharge 141. Accordingly, the apparatus 100 provides for modular determination of collected readings adjusted to minimize the effects of discharge noise.

A simplified alternative embodiment of the present invention eliminates the calibrator 62 and provides for timed collection of collected signal value 92 by sample and hold processor 64. In such alternative embodiment, the collected signal value 92 is not adjusted based on discharge signal value 82. In such alternative embodiment, the collected signal value 92 is still determined during a time window determined by sample and hold processor 64 circuitry or microprocessor. This alternative embodiment provides the advantages of modular collection of collected signal value 92.

The foregoing disclosure and description of the invention is illustrative and explanatory thereof. Various changes in the details of the illustrated construction may be made within the scope of the appended claims without departing from the spirit of the invention. The present invention should only be limited by the following claims and their legal equivalents.

What is claimed is:

1. A pulsed discharge detector having a discharge source and a collector, said detector comprising:

an electrometer;

a calibrator;

said electrometer electrically connected to said collector and to said calibrator;

a discharge monitor electrically connected to said discharge source and to said calibrator;

said electrometer detecting a collector signal;

said electrometer generating a collected signal value proportional to said collector signal;

said discharge monitor detecting a discharge signal;

said discharge monitor generating at least one discharge signal value proportional to said discharge signal; and said calibrator receiving said at least one discharge signal value.

2. The detector as in claim 1 wherein:

said at least one discharge signal value including a discharge signal intensity value; and said calibrator adjusting said collected signal value proportional to said discharge signal intensity value.

3. The detector as in claim 2 further comprising:

said calibrator electrically connected to a processor;

said calibrator generating an adjusted signal value proportional to said adjusted collected value; and said processor accumulating at least one characteristic of said adjusted collected value.

4. The detector as in claim 3 wherein:

said processor electrically connected to said discharge monitor;

said processor receiving a discharge time value from said discharge monitor; and said processor receiving said adjusted signal value during a time window initiated in response to said discharge time value.

5. The detector as in claim 1 wherein:

said at least one discharge signal value including a discharge time value; and said calibrator processing said collected signal value during a time window initiated in response to said discharge time value.

6. The detector as in claim 1 wherein:

said collector signal comprises a measure of ions received at said collector.

7. The detector as in claim 1 further comprising:

a bias voltage generator;

said bias voltage generator electrically connected to said collector and said electrometer.

8. A pulsed discharge detector having a discharge source and a collector, said detector comprising:

an electrometer;

a processor;

said electrometer electrically connected to said collector and to said sample and hold processor;

a discharge monitor electrically connected to said discharge source and to signal and hold processor;

said electrometer detecting a collector signal;

said electrometer generating a collected signal value proportional to said collector signal;

said discharge monitor detecting a discharge signal;

said discharge monitor generating a discharge time value proportional to said discharge signal; and said processor receiving said collected signal value during a time window initiated in response to said discharge time value.

9. The detector as in claim 8 further comprising:

a bias voltage generator;

said bias voltage generator electrically connected to said collector and said electrometer.

10. A detector for quantities of matter in a carrier gas comprising:

a closed chamber;

a discharge gas inlet, a sample gas inlet and a gas vent each accessing said closed chamber;

an electrical discharge source in said chamber;

a discharge monitor electrically monitoring said discharge source;

said discharge monitor producing a discharge signal value;

a collector within said chamber;

an electrometer electrically monitoring said collector;

said electrometer producing a collected signal value proportional to ionized atoms contacting said collector;

a calibrator electrically connected to said electrometer and said discharge monitor; and said calibrator adjusting said collected signal value for variations in said discharge signal value.

11. The detector of claim 10 further comprising:

said closed chamber defined by an elongated chamber wall, a discharge end and a collector end;

said elongated chamber wall defining a cylinder at said discharge end;

said elongated chamber wall defining a cylinder at said collector end;

said closed chamber having a central chamber axis;

said discharge source comprising a discharge electrode and a receptor electrode proximate said discharge end;

said discharge electrode oriented at said central chamber axis;

said receptor electrode in said elongated chamber wall proximate said discharge electrode;

said collector proximate said collector end; and said collector oriented at said central chamber axis.

12. The detector of claim 11 wherein:

said discharge gas inlet accessing said closed chamber proximate said discharge end;

said sample gas inlet accessing said closed chamber intermediate said discharge electrode and said collector; and said gas vent accessing said closed chamber proximate said collector end.

13. The detector of claim 12 wherein:

said closed chamber having a discharge end diameter;

said closed chamber having a collector end diameter; and said collector end diameter larger than said discharge end diameter.

14. The detector of claim 13 wherein:

said elongated chamber wall comprising a truncated conical chamber wall intermediate said discharge end and said collector end; and said sample gas inlet accessing said closed chamber at said truncated conical chamber wall.

15. The detector of claim 11 further comprising:

said discharge monitor electrically connected to said receptor electrode;

said electrometer electrically connected to said collector;

said calibrator electrically connected to said discharge monitor and said electrometer; and a processor receiving an adjusted signal value from said calibrator.

16. The detector as in claim 15 wherein:

said electrical source is intermittently dischargeable;

said discharge monitor transmitting a discharge time signal to said processor; and said processor receiving said adjusted signal value at a time determined in relation to said discharge time signal.

17. The detector as in claim 16 wherein:

said discharge monitor transmitting a discharge intensity value signal to said calibrator; and said calibrator calibrating said collected signal value proportional to said discharge intensity signal value.

18. A device for processing collected values from a pulsed discharge detector having a pulsed discharge source and a collector, comprising:

an electrometer;

a calibrator;

said electrometer electrically connected to said collector and to said calibrator;

a discharge monitor electrically connected to said pulsed discharge source and to said calibrator;

said electrometer detecting a collector signal;

said electrometer generating a collected signal value proportional to said collector signal;

said discharge monitor detecting a discharge signal;

said discharge monitor generating at least one discharge signal value proportional to said discharge signal; and said calibrator receiving said at least one discharge signal value.

19. The device as in claim 18 wherein:

said at least one discharge signal value including a discharge signal intensity value; and said calibrator adjusting said collected signal value proportional to said discharge signal intensity value.

20. The device as in claim 19 further comprising:

said calibrator electrically connected to a processor;

said calibrator generating an adjusted signal value proportional to said adjusted collected signal value; and said processor accumulating at least one characteristic of said adjusted collected signal value.

21. The device as in claim 20 wherein:

said processor electrically connected to said discharge monitor;

said processor receiving a discharge time value from said discharge monitor; and said processor receiving said adjusted collected signal value during a time window initiated in response to said discharge time value.

22. The device as in claim 21 further comprising:

a bias voltage generator;

said bias voltage generator electrically connected to said collector and said electrometer.

23. The device as in claim 18 wherein:

said at least one discharge signal value including a discharge time value; and said calibrator processing said collected signal value during a time window initiated in response to said discharge time value.

24. A method for processing collected signals from a pulsed discharge detector having a pulse discharge source and a collector, comprising:

monitoring a pulse discharge intensity value;

determining a value of electrons impinging a collector of said pulsed discharge detector during a determined time period; and adjusting said collected signal based on at least one said pulse discharge intensity value.

25. The method as in claim 24 further comprising:

monitoring a pulse discharge time value; and adjusting said collected signal during a time window determined in relation to said pulse discharge time value.

26. The method as in claim 25 further comprising:

transmitting selected characteristics of said adjusted collected signal to a processor during a time period determined in relation to said pulse discharge time value.

27. A method for measuring a characteristic of a sample gas comprising:

flowing a discharge gas through a closed chamber;

producing photons from said discharge gas by exposing said discharge gas to a plurality of discharges;

monitoring a discharge value of each of said plurality of discharges;

introducing a sample gas into the flow of said discharge gas and said photons in said closed chamber to ionize at least part of said sample gas;

measuring a quantity of ions produced in said sample gas from each of said plurality of discharges; and adjusting each of said measured quantity of ions based on each of said discharge values.

28. The method as in claim 27 further comprising:

monitoring an occurrence time of each of said discharge values; and adjusting each of said measured quantity of ions during a time window determined in relation to each of said discharge occurrence time times.

29. The method as in claim 28 further comprising:

collecting a selected characteristic of each of said adjusted measured quantity of ions during a time window determined in relation to each of said discharge occurrence time.

* * * * *